United States Patent
Lee et al.

(10) Patent No.: US 11,510,884 B2
(45) Date of Patent: Nov. 29, 2022

(54) BOWEL CLEANSING COMPOSITION

(71) Applicant: TAEJOON PHARMACEUTICAL CO., LTD., Seoul (KR)

(72) Inventors: Joon Youb Lee, Seoul (KR); Woo Young Jang, Suwon-Si (KR); Yiseul Song, Suwon-Si (KR)

(73) Assignee: TAEJOON PHARMACEUTICAL CO., LTD.

( * ) Notice: Subject to any disclaimer, the term of this patent is extended or adjusted under 35 U.S.C. 154(b) by 47 days.

(21) Appl. No.: 16/965,182

(22) PCT Filed: Feb. 1, 2019

(86) PCT No.: PCT/KR2019/001456
§ 371 (c)(1),
(2) Date: Jul. 27, 2020

(87) PCT Pub. No.: WO2019/151829
PCT Pub. Date: Aug. 8, 2019

(65) Prior Publication Data
US 2021/0052510 A1  Feb. 25, 2021

(30) Foreign Application Priority Data

Feb. 1, 2018 (KR) .................. 10-2018-0013113
Jun. 8, 2018 (KR) .................. 10-2018-0066282
Oct. 8, 2018 (KR) .................. 10-2018-0119830
Jan. 9, 2019 (KR) .................. 10-2019-0002739

(51) Int. Cl.
*A61K 31/047* (2006.01)
*A61K 9/08* (2006.01)
*A61K 31/375* (2006.01)
*A61K 33/14* (2006.01)

(52) U.S. Cl.
CPC .......... *A61K 31/047* (2013.01); *A61K 9/08* (2013.01); *A61K 31/375* (2013.01); *A61K 33/14* (2013.01)

(58) Field of Classification Search
CPC .......... A61K 2300/00; A61K 31/365; A61K 31/375; A61K 33/14; A61K 31/047; A61K 31/765; A61K 9/08; A61P 1/10
See application file for complete search history.

(56) References Cited

U.S. PATENT DOCUMENTS

| 5,274,001 A | 12/1993 | Borody |
| 7,169,381 B2 | 1/2007 | Barras et al. |
| 2014/0010895 A1* | 1/2014 | Halphen .............. A61K 31/765 |
| | | 424/679 |

FOREIGN PATENT DOCUMENTS

| JP | 2008-001724 | 1/2008 |
| KR | 10-2007-0001280 | 1/2007 |
| KR | 10-2012-0070560 | 6/2012 |
| KR | 10-2014-0010117 | 1/2014 |
| KR | 10-2014-0044628 | 4/2014 |
| KR | 10-2015-0054990 | 5/2015 |
| KR | 10-1771586 | 8/2017 |
| RU | 2600790 C2 | 8/2022 |
| WO | WO 2004/037292 | 5/2004 |
| WO | WO 2005/102364 | 11/2005 |
| WO | WO 2011/007153 | 1/2011 |
| WO | WO 2012/123720 | 9/2012 |
| WO | WO 2014/040994 | 3/2014 |
| WO | WO 2014/054880 | 4/2014 |

OTHER PUBLICATIONS

English translation of International Search Report issued in International Application No. PCT/KR2019/001456, dated May 13, 2019.
Office Communication issued in Korean Patent Application No. 10-2018-0119830, dated Nov. 18, 2018. (English translation of Korean text).
Office Communication issued in Korean Patent Application No. 10-2018-0119830, dated Mar. 28, 2019. (English translation of Korean text).
International Search Report issued in International Application No. PCT/KR2019/001456, dated Feb. 1, 2019. (English translation of Russian text).
Mínguez M, López Higueras A, Júdez J. Use of polyethylene glycol in functional constipation and fecal impaction. Rev Esp Enferm Dig. Dec. 2016;108(12):790-806.
Office Communication issued in Russian Patent Application No. 2020128710, dated Aug. 9, 2022. (English translation of Russian text).
Soh JS, Kim KJ. Combination could be another tool for bowel preparation? World J Gastroenterol. Mar. 14, 2016;22(10):2915-21.

* cited by examiner

*Primary Examiner* — Umamaheswari Ramachandran
(74) *Attorney, Agent, or Firm* — ParkerHighlander, PLLC

(57) ABSTRACT

The present invention relates to a bowel cleansing composition comprising polyethylene glycol and ascorbate ingredients, the bowel cleansing composition of the present invention being easier to take, while having an excellent bowel cleansing effect, thereby being usable as an effective bowel cleansing agent.

25 Claims, 2 Drawing Sheets

[Figure 1]
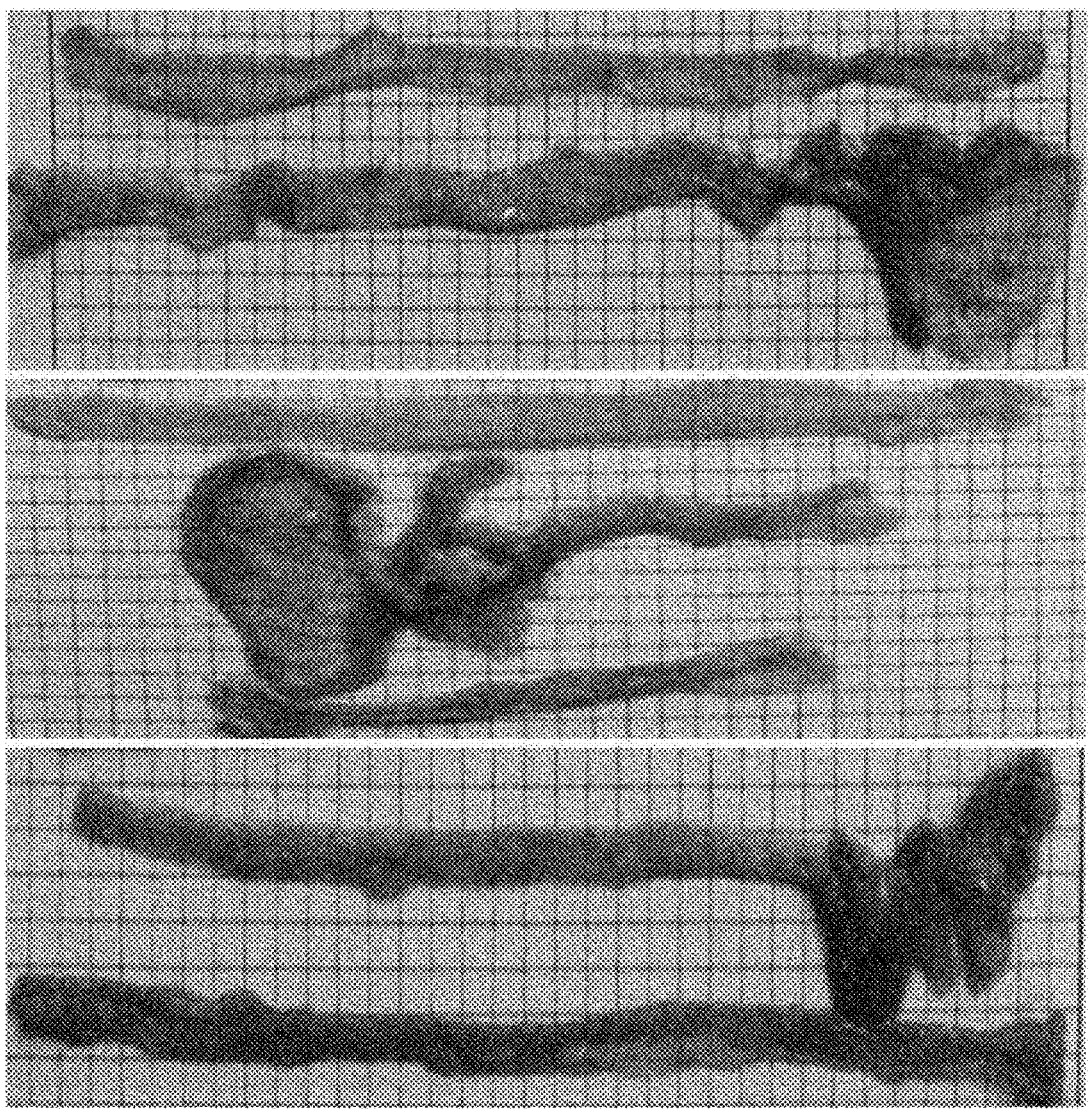

【Figure 2】
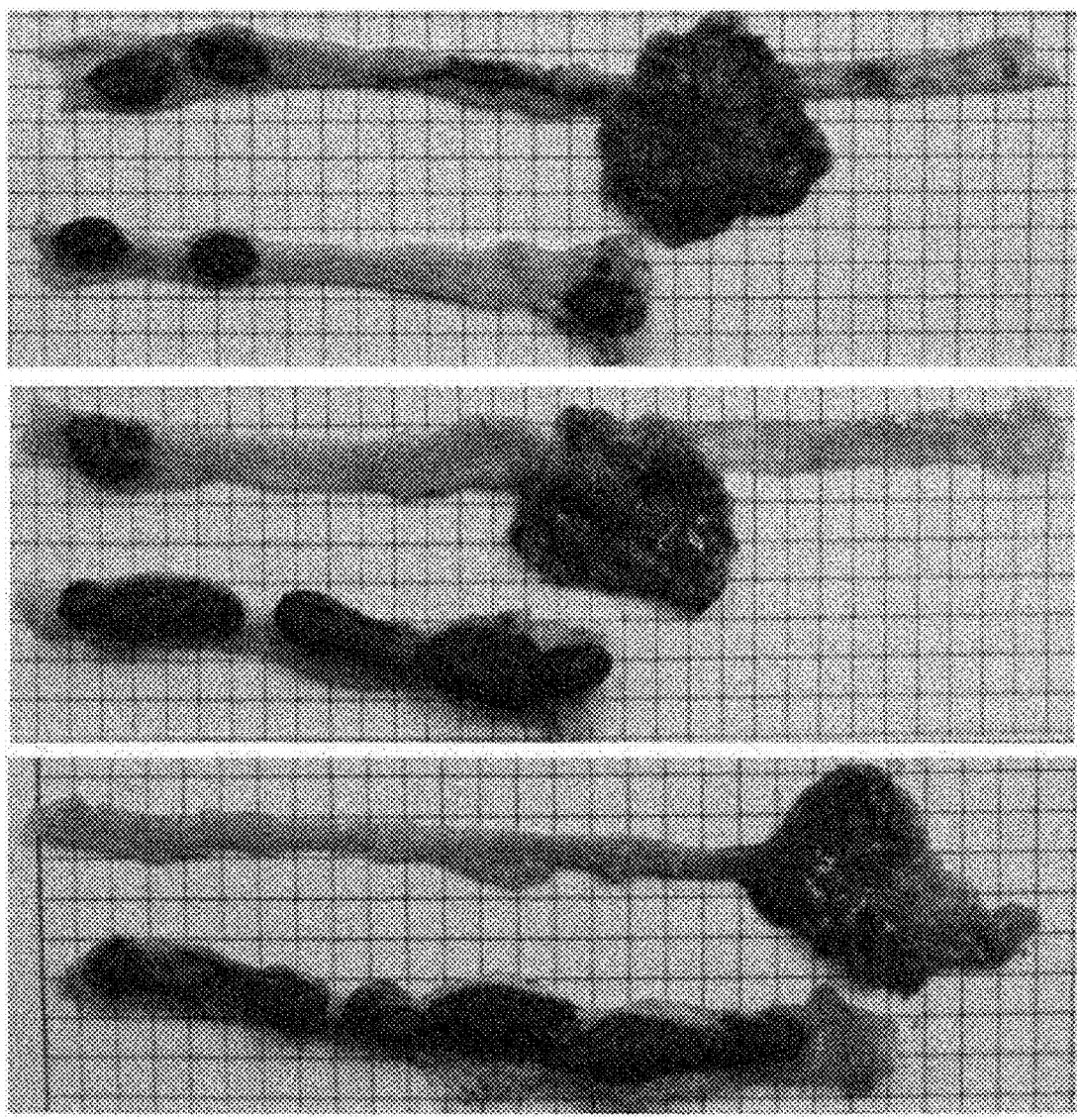

BOWEL CLEANSING COMPOSITION

This application is a national phase application under 35 U.S.C. § 371 of International Application No. PCT/KR2019/001456, filed Feb. 1, 2019, which claims the benefit of Korean Patent Application No. 10-2019-0002739, filed Jan. 9, 2019, Korean Patent Application No. 10-2018-0119830, filed Oct. 8, 2018, Korean Patent Application No. 10-2018-0066282, filed Jun. 8, 2018 and Korean Patent Application No. 10-2018-0013113, filed Feb. 1, 2018. The entirety of each of which is incorporated herein by reference.

TECHNICAL FIELD

The present invention relates to a bowel cleansing composition comprising polyethylene glycol and ascorbate ingredients.

BACKGROUND ART

Colorectal cancer is a cancer that has shown a steady increase in incidence rate until now since the 1980s. According to the main causes of death reported by the National Statistical Office in 2016, the number of deaths caused by colorectal cancer is higher than the number of deaths caused by gastric cancer, and colorectal cancer is considered as one of the top three cancers leading to death along with lung cancer and liver cancer.

Colorectal cancer is difficult to detect early because there are no particular symptoms. Thus, it is necessary to undergo colonoscopy regularly. According to the recommendation of the Ministry of Health and Welfare, they recommends that the test be conducted at least every five years for people over 50 years old.

In order to increase the accuracy of colonoscopy, it is essential that the intestines be washed before the test, which is usually done by the patient taking the bowel cleansing agent at home. Thus, the patients should not be confused or difficult in taking the bowel cleansing agent for themselves, should not have any difficulty in taking all the bowel cleansing agent, and serious side effects should not occur due to such taking.

Meanwhile, the representative bowel cleansing agent comprising polyethylene glycol, which is a representative ingredients of the bowel cleansing agent, include GoLytely and NuLytely products of Braintree. However, in order to achieve a bowel cleansing effect using the products, all 4 L of liquid medicine should be taken, and the products have a taste that is difficult to take, such as salty taste, repulsive taste, etc. In particular, since the amount of the liquid medicine to be taken is too high to take, many patients failed to take the bowel cleansing agent even before performing the colonoscopy, the test was not properly performed. Furthermore, when taking 4 L of the liquid medicine, there were problems about side effects such as nausea, vomiting, etc.

In order to solve the above problems, products of GLYCOPREP and Moviprep with reduced doses of the liquid medicine have been developed by including ascorbate ingredients. However, even using the above products, the total volume of the liquid to be taken was 3 L, which was still not easy to take and there was a problem of low patient compliance.

In particular, as a digestive-related side effects that can be caused by taking a large amount of the liquid medicine in a short time, it has been reported that there are nausea, abdominal pain, absorption of solution in patients with gastric outlet obstruction, toxic colitis, etc. In addition, side effects may worsen in patients suspected of intestinal obstruction. Thus, the guideline for bowel cleansing instructs to continue when there is no problem after taking 1 L of the liquid medicine. Thus, there is still a need for development of a bowel cleansing agent that can achieve the convenience of taking and a bowel cleansing effect while reducing the dose.

Accordingly, the present inventors have tried to solve the above problems, thereby completing a safe bowel cleansing composition, which shows an excellent bowel cleansing effect while reducing the dose of the liquid medicine, and which can easily take a considerable amount of the liquid medicine required as a bowel cleansing agent.

DISCLOSURE

Technical Problem

It is an object of the present invention to provide a bowel cleansing composition comprising polyethylene glycol and ascorbate ingredients.

Technical Solution

In one aspect for achieving the objective, the present invention provides a bowel cleansing composition comprising polyethylene glycol (PEG) and ascorbate ingredients.

Also, in another aspect for achieving the objective, the present invention provides a bowel cleansing solution comprising polyethylene glycol (PEG) and ascorbate ingredients.

A content of ingredients contained in the bowel cleansing composition and the bowel cleansing solution of the present invention may be expressed in units of g (gram), mole, g/L, M (molarity), and the like.

The average molecular weight of polyethylene glycol (PEG) of the present invention may be the average molecular weight of conventional polyethylene glycol used in the bowel cleansing composition or the bowel cleansing solution, it may be 100 to 10,000, but is not limited thereto. As one example, the average molecular weight of polyethylene glycol may be 2,000 to 8,000, specifically 2,000 to 5,000, and more specifically 3,000 to 4,000. The polyethylene glycol of the present invention may be polyethylene glycol 3350 (PEG3350) or polyethylene glycol 4000 (PEG4000).

The content of polyethylene glycol contained in the bowel cleansing composition of the present invention may be 55 mmol or less, specifically 50 mmol or less. In addition, the content of polyethylene glycol may be 40 mmol or more, specifically 45 mmol or more. The content of polyethylene glycol contained in the bowel cleansing composition of the present invention may be 40 to 55 mmol, specifically 45 to 50 mmol, and more specifically 47.76 mmol.

The content of polyethylene glycol contained in the bowel cleansing composition of the present invention may be 180 g or less, specifically 170 g or less. In addition, the content of polyethylene glycol may be 140 g or more, specifically 150 g or more. The content of polyethylene glycol contained in the bowel cleansing composition of the present invention may be 140 to 180 g, specifically 150 to 170 g, and more specifically 160 g.

When the average molecular weight of polyethylene glycol contained in the bowel cleansing composition of the present invention is 3,350, that is, polyethylene glycol 3350, the content of polyethylene glycol 3350 may be 180 g or less, specifically 170 g or less. In addition, the content of polyethylene glycol 3350 may be 140 g or more, specifically 150 g or more. The content of polyethylene glycol 3350 contained in the bowel cleansing composition of the present invention may be 140 to 180 g, specifically 150 to 170 g, and more specifically 160 g.

The content (g) of polyethylene glycol contained in the bowel cleansing composition of the present invention may vary depending on the average molecular weight of polyethylene glycol.

When the bowel cleansing composition of the present invention is provided as a bowel cleansing solution, the content of polyethylene glycol contained in the bowel cleansing solution may be 55 mM or less, specifically 50 mM or less. In addition, the content of polyethylene glycol may be 40 mM or more, specifically 45 mM or more. The content of polyethylene glycol contained in the bowel cleansing solution of the present invention may be 40 to 55 mM, specifically 45 to 50 mM, and more specifically 47.76 mM.

When the bowel cleansing composition of the present invention is provided as a bowel cleansing solution, the content of polyethylene glycol contained in the bowel cleansing solution may be 180 g/L or less, specifically 170 g/L or less. In addition, the content of polyethylene glycol may be 140 g/L or more, specifically 150 g/L or more. The content of the polyethylene glycol contained in the bowel cleansing solution of the present invention may be 140 to 180 g/L, specifically 150 to 170 g/L, and more specifically 160 g/L.

When the bowel cleansing composition of the present invention is provided as a bowel cleansing solution comprising polyethylene glycol 3350, the content of polyethylene glycol 3350 contained in the bowel cleansing solution may be 180 g/L or less, specifically 170 g/L or less. In addition, the content of polyethylene glycol 3350 may be 140 g/L or more, specifically 150 g/L or more. The content of polyethylene glycol 3350 contained in the bowel cleansing solution of the present invention may be 140 to 180 g/L, specifically 150 to 170 g/L, and more specifically 160 g/L.

The content (g/L) of polyethylene glycol contained in the bowel cleansing composition of the present invention may vary depending on the average molecular weight of polyethylene glycol.

The polyethylene glycol contained in the bowel cleansing composition and the bowel cleansing solution of the present invention should be contained in an amount to exert a sufficient bowel cleansing effect. If contained more than the amount, a taste of a bowel cleansing agent may become bad, thereby causing a problem of decreasing compliance to and convenience of taking, and also an osmotic pressure of the bowel cleansing agent may become excessively higher, thereby causing a safety problem.

The ascorbate ingredients of the present invention contain ascorbic acid and/or salts of ascorbic acid, and may specifically contain both ascorbic acid and salts of ascorbic acid. The molecular weight of ascorbic acid may be 176 g/mol. The salts of ascorbic acid contained in the bowel cleansing composition or the bowel cleansing solution of the present invention may be contained in the form of an alkali metal salt and/or alkaline earth metal salt. Specific types of the salts of ascorbic acid may be any one or more selected from the group consisting of salts of sodium, salts of potassium, salts of magnesium and salts of calcium, but are not limited thereto. Specifically, the salts of ascorbic acid may be sodium ascorbate (molecular weight of 198 g/mol). The ascorbate ingredients contained in the bowel cleansing composition or the bowel cleansing solution of the present invention may be contained in the form of ester ascorbic acid fatty acid ester, and may be used with the addition of a surfactant component for solubilizing it.

The content of ascorbate ingredients contained in the bowel cleansing composition of the present invention may be less than 300 mmol, specifically 290 mmol or less. In addition, the content of ascorbate ingredients may be 250 mmol or more, specifically 270 mmol or more. The content of ascorbate ingredients contained in the bowel cleansing composition of the present invention may be 250 mmol or more and less than 300 mmol, specifically 270 to 290 mmol, and more specifically 278.16 mmol.

The content of ascorbate ingredients contained in the bowel cleansing composition of the present invention may be less than 55 g, specifically 54 g or less, and more specifically 53 g or less. In addition, the content of ascorbate ingredients may be 45 g or more, specifically 48 g or more. The content of ascorbate ingredients contained in the bowel cleansing composition of the present invention may be 45 g or more and less than 55 g, specifically 45 to 54 g, specifically 48 to 53 g, and more specifically 50 g.

When the bowel cleansing composition of the present invention is provided as a bowel cleansing solution, the content of ascorbate ingredients contained in the bowel cleansing solution may be less than 300 mM, specifically 290 mM or less. In addition, the content of ascorbate ingredients may be 250 mM or more, specifically 270 mM or more. The content of ascorbate ingredients contained in the bowel cleansing solution of the present invention may be 250 mM or more and less than 300 mM, specifically 270 to 290 mM, and more specifically 278.16 mM.

When the bowel cleansing composition of the present invention is provided as a bowel cleansing solution, the content of ascorbate ingredients contained in the bowel cleansing solution may be less than 55 g/L, specifically 54 g/L or less, and more specifically 53 g/L or less. In addition, the content of ascorbate ingredients may be 45 g/L or more, specifically 48 g/L or more. The content of ascorbate ingredients contained in the bowel cleansing solution of the present invention may be 45 g/L or more and less than 55 g/L, specifically 45 to 54 g/L, specifically 48 to 53 g/L, and more specifically 50 g/L.

The ascorbate ingredients may have a toxicity problems such as kidney trouble when excessively taken, and may cause nausea, retching, heartburn and the like due to irritation of the stomach. Thus, the ascorbate ingredients of the present invention may be contained within the above range, and it may be preferable that the content of ascorbate ingredients is 53 g/L or less, more specifically 50 g/L or less.

It is important to adjust the content ratio between polyethylene glycol and ascorbate ingredients in order to enhance the bowel cleansing effect and safety of the bowel cleansing composition or the bowel cleansing solution of the present invention. The molar ratio between polyethylene glycol and ascorbate ingredients contained in the bowel cleansing composition or the bowel cleansing solution of the present invention may be 1:4.5 to 1:7.5, specifically 1:5.5 to 1:6, and more specifically 1:5.82. The weight ratio between polyethylene glycol and ascorbate ingredients contained in the bowel cleansing composition or the bowel cleansing solution of the present invention may be 2.5:1 to 4:1, specifically 3:1 to 3.5:1, and more specifically 3.2:1.

Depending on the content ratio between polyethylene glycol and ascorbate ingredients in the bowel cleansing composition or the bowel cleansing solution of the present invention, the bowel cleansing composition or the bowel cleansing solution of the present invention not only exhibits an excellent bowel cleansing effect, but also exhibits an excellent safety with improved mucosal damage and the change of numerical value on blood test. In one embodiment, the bowel cleansing solution of the present invention is that in an animal experiments compared to a bowel cleansing solution with a higher weight ratio of ascorbate ingredients to polyethylene glycol, the mortality; gastric mucosal damage; and the change of the concentration of asparate aminotransferase (AST), alkaine aminotransferase (ALT), blood urea nitrogen (BUN), creatinine, red blood cell (RBC), hemoglobin (HGB), mean corpuscular hemoglobin concentration (MCHC), hematocrit (HCT) and the like in blood test are significantly low, and thus it was confirmed that they are a bowel cleansing solution with an excellent safety (see Experimental Example 2, etc.).

The ascorbate ingredients of the present invention may include ascorbic acid, salts of ascorbic acid or a mixtures thereof. It is preferable that the ascorbate ingredients of the present invention include both ascorbic acid and salts of ascorbic acid. The salts of ascorbic acid may be sodium ascorbate.

When the bowel cleansing composition of the present invention contains ascorbic acid and salts of ascorbic acid, the content of ascorbic acid may be 255 mmol or less, specifically 240 mmol or less, and the content of salts of ascorbic acid may be 55 mmol or less, specifically 50 mmol or less. In addition, the content of ascorbic acid may be 200 mmol or more, specifically 220 mmol or more, and the content of salts of ascorbic acid may be 40 mmol or more, specifically 45 mmol or more. The content of ascorbic acid contained in the bowel cleansing composition of the present invention comprising ascorbic acid and salts of ascorbic acid may be 200 to 255 mmol, specifically 220 to 240 mmol, and more specifically 230.68 mmol, and the content of salts of ascorbic acid may be 40 to 55 mmol, specifically 45 to 50 mmol, and more specifically 47.47 mmol.

When the bowel cleansing composition of the present invention contains ascorbic acid and sodium ascorbate, the content of ascorbic acid may be 45 g or less, specifically 43 g or less, and the content of sodium ascorbate may be 11 g or less, specifically 10 g or less. In addition, the content of ascorbic acid may be 35 g or more, specifically 39 g or more, and the content of sodium ascorbate may be 8 g or more, specifically 9 g or more. The content of ascorbic acid contained in the bowel cleansing composition of the present invention comprising ascorbic acid and sodium ascorbate may be 35 to 45 g, specifically 39 to 43 g, and more specifically 40.6 g. The content of sodium ascorbate may be 8 to 11 g, specifically 9 to 10 g, and more specifically 9.4 g.

When ascorbic acid and salts of ascorbic acid are contained, the salts of ascorbic acid contained in the bowel cleansing composition of the present invention may be contained in an appropriate range of content (g, g/L) depending on the form of the salts of ascorbic acid.

When the bowel cleansing composition of the present invention is provided as a bowel cleansing solution comprising ascorbic acid and salts of ascorbic acid, the content of the ascorbic acid contained in the bowel cleansing solution may be 255 mM or less, specifically 240 mM or less, and the content of salts of ascorbic acid may be 55 mM or less, specifically 50 mM or less. In addition, the content of ascorbic acid may be 200 mM or more, specifically 220 mM or more, and the content of salts of ascorbic acid may be 40 mM or more, specifically 45 mM or more. The content of ascorbic acid contained in the bowel cleansing solution of the present invention comprising ascorbic acid and salts of ascorbic acid may be 200 to 255 mM, specifically 220 to 240 mM, and more specifically 230.68 mM, and the content of salts of ascorbic acid may be 40 to 55 mM, specifically 45 to 50 mM, and more specifically 47.47 mM.

When the bowel cleansing composition of the present invention is provided as a bowel cleansing solution comprising ascorbic acid and sodium ascorbate, the content of ascorbic acid contained in the bowel cleansing solution may be 45 g/L or less, specifically 43 g/L or less, and the content of sodium ascorbate may be 11 g/L or less, specifically 10 g/L or less. In addition, the content of ascorbic acid may be 35 g/L or more, specifically 39 g/L or more, and the content of sodium ascorbate may be 8 g/L or more, specifically 9 g/L or more. The content of ascorbic acid contained in the bowel cleansing solution comprising ascorbic acid and sodium ascorbate of the present invention may be 35 to 45 g/L, specifically 39 to 43 g/L, and more specifically 40.6 g/L, and the content of sodium ascorbate may be 8 to 11 g/L, specifically 9 to 10 g/L, and more specifically 9.4 g/L.

The molar ratio between ascorbic acid and salts of ascorbic acid contained as an ascorbate ingredients of the bowel cleansing composition or the bowel cleansing solution of the present invention may be 4:1 to 6:1, specifically 4:1 to 5:1, more specifically 4.5:1 to 5:1, and even more specifically 4.8:1 to 4.9:1.

The weight ratio between ascorbic acid and sodium ascorbate contained as an ascorbate ingredients of the bowel cleansing composition or the bowel cleansing solution of the present invention may be 3.5:1 to 5:1, specifically 4:1 to 5:1, more specifically 4:1 to 4.5:1, and even more specifically 4.2:1 to 4.4:1.

Depending on the certain content ratio between ascorbic acid and sodium ascorbate contained in the bowel cleansing composition or the bowel cleansing solution of the present invention, the bowel cleansing solution of the present invention may be used as a bowel cleansing agent with excellent safety due to remarkably low numerical changes in a blood test with regard to $Na^+$, asparate aminotransferase (AST), alkaine aminotransferase (ALT), etc. in the blood. In one embodiment, it was confirmed that the bowel cleansing solution of the present invention is a solution with excellent safety due to remarkably low changes in AST levels, Na+ levels and the like in the blood, in an animal test compared to a bowel cleansing solution having a content ratio of sodium ascorbate higher than that of the bowel cleansing solution of the present invention, while containing the same content of polyethylene glycol and ascorbate ingredients (see Example 2, etc.).

The bowel cleansing composition or the bowel cleansing solution of the present invention contains ascorbic acid and salts of ascorbic acid in the range as above to exhibit an excellent bowel cleansing effect, and may also improve a taste of the bowel cleansing solution to reduce a sense of difference and a feel of repulsion when taking the solution, and may achieve convenience of taking which may facilitate taking a large amount of the solution necessary to achieve the sufficient bowel cleansing effect.

The present invention provides the bowel cleansing composition or the bowel cleansing solution comprising polyethylene glycol, ascorbate ingredients, and sulfate.

The descriptions of polyethylene glycol and ascorbate ingredients, content and concentration thereof and the like contained in the composition or solution are the same as described above.

Sulfate of the present invention may be contained in the form of alkali metal salts and/or alkaline earth metal salts thereof. The sulfate may be any one or more selected from the group consisting of sodium sulfate, potassium sulfate and magnesium sulfate, but is not limited thereto. The sulfate may be sodium sulfate, and sulfate such as sodium sulfate may be an anhydride or a hydrate. Specifically, the sulfate of the present invention may be sulfate anhydride.

As one example of the sulfate, the content of sodium sulfate in the present invention is described based on the content of sodium sulfate anhydrous (molecular weight of 142 g/mol). For sodium sulfate hydrate, the content of sodium sulfate hydrate may vary depending on the molecular weight. For example, the content of sodium sulfate is 10 g as an anhydride and 10 g of sodium sulfate as an anhydride means that sodium sulfate anhydrous is 10 g and sodium sulfate heptahydrate (molecular weight of 268 g/mol) is 18.87 g. In other words, the content of sodium sulfate hydrate is calculated in consideration of the molecular weight of the hydrate in order to obtain 10 g in the form of anhydride.

The sulfate is contained in the bowel cleansing composition or the bowel cleansing solution of the present invention to exhibit a bowel cleansing effect, and the sulfate ions generated from the sulfate can inhibit the intestinal absorption of sodium ions and minimize the absorption and excretion of water and electrolytes.

The content of sulfate contained in the bowel cleansing composition of the present invention may be 140 mmol or less, specifically 130 mmol or less. In addition, the content of sulfate may be 110 mmol or more, specifically 120 mmol or more. The content of sulfate contained in the bowel cleansing composition of the present invention may be 110 to 140 mmol, specifically 120 to 130 mmol, and more specifically 126.76 mmol.

When the sulfate contained in the bowel cleansing composition of the present invention is sodium sulfate, the content of sodium sulfate may be 20 g or less as an anhydride, specifically 18.5 g or less. In addition, the content of sodium sulfate may be 16 g or more as an anhydride, specifically 17.5 g or more. The content of sodium sulfate contained in the bowel cleansing composition of the present invention may be 16 to 20 g as an anhydride, specifically 17.5 to 18.5 g, and more specifically 18 g.

However, the content (g) of sulfate is not limited to the above range, and may be contained in an appropriate range depending on the form of sulfate contained.

When the bowel cleansing composition of the present invention is provided as a bowel cleansing solution, the content of sulfate contained in the bowel cleansing solution may be 140 mM or less, specifically 130 mM or less. In addition, the content of sulfate may be 110 mM or more, specifically 120 mM or more. The content of sulfate contained in the bowel cleansing solution of the present invention may be 110 to 140 mM, specifically 120 to 130 mM, and more specifically 126.76 mM.

When the bowel cleansing composition of the present invention is provided as a bowel cleansing solution comprising sodium sulfate, the content of sodium sulfate contained in the bowel cleansing solution may be 20 g/L or less as an anhydride, specifically 18.5 g/L or less. In addition, the content of sodium sulfate may be 16 g/L or more as an anhydride, specifically 17.5 g/L or more. The content of sodium sulfate contained in the bowel cleansing solution comprising sodium sulfate of the present invention may be 16 to 20 g/L as an anhydride, specifically 17.5 to 18.5 g/L, and more specifically 18 g/L.

The sulfate contained in the bowel cleansing composition or the bowel cleansing solution of the present invention may be contained in a molar ratio 2 to 3.5 times, specifically 2.5 to 3 times, and more specifically 2.65 times compared to polyethylene glycol, in consideration of the bowel cleansing effect and safety. In addition, the weight ratio between polyethylene glycol and sodium sulfate contained in the bowel cleansing composition or the bowel cleansing solution of the present invention may be 7:1 to 12:1, specifically 8:1 to 10:1, more specifically 8.5:1 to 9.5:1, and even more specifically 8.89:1.

When the content ratio of polyethylene glycol and sulfate contained in the bowel cleansing solution of the present invention is used, it has an advantage that the bowel cleansing effect is much better than the bowel cleansing solution having a different content ratio, and the change of numerical value on the blood test is less, thereby ensuring safety.

The present invention provides the bowel cleansing composition or the bowel cleansing solution comprising polyethylene glycol, ascorbate ingredient, sulfate, and electrolytes.

The solution provided by the bowel cleansing composition or the bowel cleansing solution has a large volume (dose) taken by the patients, and thus it may comprise an electrolytes in an appropriate range of content and/or concentration in order to reduce the absorption or loss of electrolytes and secure safety for minimizing problems such as dehydration caused by taking a high volume of solution.

The descriptions of polyethylene glycol, ascorbate ingredients, and sulfate, the contents and concentrations thereof, and the like contained in the composition or solution are the same as described above.

The electrolyte of the present invention may include alkali metal salts and/or alkaline earth metal salts, and the like. The electrolyte of the present invention may one or more selected from the group consisting of salts of sodium, salts of potassium, salts of calcium, salts of magnesium, salts of chloride, salts of iodide, salts of bicarbonate and salts of carbonate, but is not limited thereto. Specifically, the electrolyte of the present invention may be sodium chloride (NaCl, molecular weight of 58.5 g/mol) and/or potassium chloride (KCl, molecular weight of 74.55 g/mol), and more specifically the electrolyte of the present invention may be sodium chloride and potassium chloride.

The content of the electrolyte contained in the bowel cleansing composition of the present invention may be 0.1 to 10 g.

The specific electrolyte contained in the bowel cleansing composition of the present invention may include sodium chloride and potassium chloride.

The content of sodium chloride contained in the bowel cleansing composition may be 3.5 g or less, specifically 3 g or less. In addition, the content of sodium chloride may be 2 g or more, specifically 2.5 g or more. The content of sodium chloride contained in the bowel cleansing composition of the present invention may be 2 to 3.5 g, specifically 2.5 to 3 g, and more specifically 2.7 g.

In addition, the content of sodium chloride contained in the bowel cleansing composition may be 60 mmol or less, specifically 50 mmol or less. In addition, the content of sodium chloride may be 35 mmol or more, specifically 40 mmol or more. The content of sodium chloride contained in the bowel cleansing composition of the present invention may be 35 to 60 mmol, specifically 40 to 50 mmol, and more specifically 46.15 mmol.

When the bowel cleansing composition of the present invention is provided as a bowel cleansing solution, the content of sodium chloride contained in the bowel cleansing solution may be 3.5 g/L or less, specifically 3 g/L or less. In addition, the content of sodium chloride may be 2 g/L or more, specifically 2.5 g/L or more. The content of sodium chloride contained in the bowel cleansing solution of the present invention may be 2 to 3.5 g/L, specifically 2.5 to 3 g/L, and more specifically 2.7 g/L.

In addition, when the bowel cleansing composition of the present invention is provided as a bowel cleansing solution, the content of sodium chloride contained in the bowel cleansing solution may be 60 mM or less, specifically 50 mM or less. In addition, the content of sodium chloride may be 35 mM or more, specifically 40 mM or more. The content of sodium chloride contained in the bowel cleansing solution of the present invention may be 35 to 60 mM, specifically 40 to 50 mM, and more specifically 46.15 mM.

The content of potassium chloride contained in the bowel cleansing composition may preferably 2 g or less, specifically 1.5 g or less, and more specifically 1.2 g or less. In addition, the content of potassium chloride may be 0.5 g or more, specifically 0.8 g or more. The content of potassium chloride contained in the bowel cleansing composition of the present invention may be 0.5 to 2 g, specifically 0.5 to 1.5 g, more specifically 0.8 to 1.2 g, and more specifically 1 g.

In addition, the content of potassium chloride contained in the bowel cleansing composition may preferably 27 mmol or less, specifically 20 mmol or less, and more specifically 16 mmol or less. In addition, the content of potassium chloride may be 7 mmol or more, specifically 10 mmol or more. The content of potassium chloride contained in the bowel cleansing solution of the present invention may be 7 to 27 mmol, specifically 7 to 20 mmol, more specifically 10 to 16 mmol, and more specifically 13.41 mmol.

When the bowel cleansing composition of the present invention is provided as a bowel cleansing solution, the content of potassium chloride contained in the bowel cleansing solution may be 2 g/L or less, specifically 1.5 g/L or less, and more specifically 1.2 g/L or less. In addition, the content of potassium chloride may be 0.5 g/L or more, specifically 0.8 g/L or more. The content of potassium chloride contained in the bowel cleansing solution of the present invention may be 0.5 to 2 g/L, specifically 0.5 to 1.5 g/L, more specifically 0.8 to 1.2 g/L, and more specifically 1 g/L.

In addition, when the bowel cleansing composition of the present invention is provided as a bowel cleansing solution, the content of potassium chloride contained in the bowel cleansing solution may be 27 mM or less, specifically 20 mM or less, and more specifically 16 mM or less. In addition, the content of potassium chloride may be 7 mM or more, specifically 10 mM or more. The content of potassium chloride contained in the bowel cleansing solution of the present invention may be 7 to 27 mM, specifically 7 to 20 mM, more specifically 10 to 16 mM, and more specifically 13.41 mM.

The bowel cleansing solution of the present invention exhibits an excellent bowel cleansing effect by adjusting the content of potassium chloride to 2 g/L or less, specifically 1 g/L or less, and contributes to providing the bowel cleansing solution with secured safety by suppressing a concentration changes in blood electrolytes (sodium, etc.).

The present invention provides the bowel cleansing composition comprising 40 to 55 mmol of polyethylene glycol, 250 mmol or more and less than 300 mmol of ascorbate ingredients, 110 to 140 mmol of sulfate, 35 to 60 mmol of sodium chloride, and 7 to 27 mmol of potassium chloride.

The present invention provides the bowel cleansing composition comprising 140 to 180 g of polyethylene glycol, 45 g or more and less than 55 g of ascorbate ingredients, 16 to 20 g of sodium sulfate as an anhydride, 2 to 3.5 g of sodium chloride, and 0.5 to 2 g of potassium chloride.

The present invention provides the bowel cleansing composition comprising 140 to 180 g of polyethylene glycol, 45 to 54 g of ascorbate ingredients, 16 to 20 g of sodium sulfate as an anhydride, 2 to 3.5 g of sodium chloride, and 0.5 to 2 g of potassium chloride.

The present invention provides the bowel cleansing solution comprising 40 to 55 mM of polyethylene glycol, 250 mM or more and less than 300 mM of ascorbate ingredients, 110 to 140 mM of sulfate, 35 to 60 mM of sodium chloride, and 7 to 27 mM of potassium chloride.

The present invention provides the bowel cleansing solution comprising 140 to 180 g/L of polyethylene glycol, 45 g/L or more and less than 55 g/L of ascorbate ingredients, 16 to 20 g/L of sodium sulfate as an anhydride, 2 to 3.5 g/L of sodium chloride, and 0.5 to 2 g/L of potassium chloride.

The present invention provides the bowel cleansing solution comprising 140 to 180 g/L of polyethylene glycol, 45 to 54 g/L of ascorbate ingredients, 16 to 20 g/L of sodium sulfate as an anhydride, 2 to 3.5 g/L of sodium chloride, and 0.5 to 2 g/L of potassium chloride.

The present invention provides the bowel cleansing composition comprising 40 to 55 mmol of polyethylene glycol, 200 to 255 mmol of ascorbic acid, 40 to 55 mmol of sodium ascorbate, 110 to 140 mmol of sulfate, 35 to 60 mmol of sodium chloride, and 7 to 27 mmol of potassium chloride.

The present invention provides the bowel cleansing composition comprising 140 to 180 g of polyethylene glycol, 35 to 45 g of ascorbic acid, 8 to 11 g of sodium ascorbate, 16 to 20 g of sodium sulfate as an anhydride, 2 to 3.5 g of sodium chloride, and 0.5 to 2 g of potassium chloride.

The present invention provides the bowel cleansing solution comprising 40 to 55 mM of polyethylene glycol, 200 to 255 mM of ascorbic acid, 40 to 55 mM of sodium ascorbate, 110 to 140 mM of sulfate, 35 to 60 mM of sodium chloride, and 7 to 27 mM of potassium chloride.

The present invention provides the bowel cleansing solution comprising 140 to 180 g/L of polyethylene glycol, 35 to 45 g/L of ascorbic acid, 8 to 11 g/L of sodium ascorbate, 16 to 20 g/L of sodium sulfate as an anhydride, 2 to 3.5 g/L of sodium chloride, and 0.5 to 2 g/L of potassium chloride.

The present invention provides the bowel cleansing composition comprising 45 to 50 mmol of polyethylene glycol, 270 to 290 mmol of ascorbate ingredients, 120 to 130 mmol of sulfate, 40 to 50 mmol of sodium chloride, and 10 to 16 mmol of potassium chloride.

The present invention provides the bowel cleansing composition comprising 150 to 170 g of polyethylene glycol, 48 to 53 g of ascorbate ingredients, 17.5 to 18.5 g of sodium sulfate as an anhydride, 2.5 to 3 g of sodium chloride, and 0.8 to 1.2 g of potassium chloride. The present invention provides the bowel cleansing solution comprising 45 to 50 mM of polyethylene glycol, 270 to 290 mM of ascorbate ingredients, 120 to 130 mM of sulfate, 40 to 50 mM of sodium chloride, and 10 to 16 mM of potassium chloride.

The present invention provides the bowel cleansing solution comprising 150 to 170 g/L of polyethylene glycol, 48 to 53 g/L of ascorbate ingredients, 17.5 to 18.5 g/L of sodium sulfate as an anhydride, 2.5 to 3 g/L of sodium chloride, and 0.8 to 1.2 g/L of potassium chloride.

The present invention provides the bowel cleansing composition comprising 45 to 50 mmol of polyethylene glycol, 220 to 240 mmol of ascorbic acid, 45 to 50 mmol of sodium ascorbate, 120 to 130 mmol of sulfate, 40 to 50 mmol of sodium chloride, and 10 to 16 mmol of potassium chloride.

The present invention provides the bowel cleansing composition comprising 150 to 170 g of polyethylene glycol, 39 to 43 g of ascorbic acid, 9 to 10 g of sodium ascorbate, 17.5 to 18.5 g of sodium sulfate as an anhydride, 2.5 to 3 g of sodium chloride, and 0.8 to 1.2 g of potassium chloride.

The present invention provides the bowel cleansing solution comprising 45 to 50 mM of polyethylene glycol, 220 to 240 mM of ascorbic acid, 45 to 50 mM of sodium ascorbate, 120 to 130 mM of sulfate, 40 to 50 mM of sodium chloride, and 10 to 16 mM of potassium chloride.

The present invention provides the bowel cleansing solution comprising 150 to 170 g/L of polyethylene glycol, 39 to 43 g/L of ascorbic acid, 9 to 10 g/L of sodium ascorbate, 17.5 to 18.5 g/L of sodium sulfate as an anhydride, 2.5 to 3 g/L of sodium chloride, and 0.8 to 1.2 g/L of potassium chloride.

The present invention provides the bowel cleansing composition comprising 47.76 mmol of polyethylene glycol 3350, 278.16 mmol of ascorbate ingredients, 126.76 mmol of sodium sulfate, 46.15 mmol of sodium chloride, and 13.41 mmol of potassium chloride.

The present invention provides the bowel cleansing composition comprising 160 g of polyethylene glycol 3350, 50 g of ascorbate ingredients, 18 g of sodium sulfate as an anhydride, 2.7 g of sodium chloride, and 1 g of potassium chloride.

The present invention provides the bowel cleansing solution comprising 47.76 mM of polyethylene glycol 3350, 278.16 mM of ascorbate ingredients, 126.76 mM of sodium sulfate, 46.15 mM of sodium chloride, and 13.41 mM of potassium chloride.

The present invention provides the bowel cleansing solution comprising 160 g/L of polyethylene glycol 3350, 50 g/L of ascorbate ingredients, 18 g/L of sodium sulfate as an anhydride, 2.7 g/L of sodium chloride, and 1 g/L of potassium chloride.

The present invention provides the bowel cleansing composition comprising 47.76 mmol of polyethylene glycol 3350, 230.68 mmol of ascorbic acid, 47.47 mmol of sodium ascorbate, 126.76 mmol of sodium sulfate, 46.15 mmol of sodium chloride, and 13.41 mmol of potassium chloride.

The present invention provides the bowel cleansing composition comprising 160 g of polyethylene glycol 3350, 40.6 g of ascorbic acid, 9.4 g of sodium ascorbate, 18 g of sodium sulfate as an anhydride, 2.7 g of sodium chloride, and 1 g of potassium chloride.

The present invention provides the bowel cleansing solution comprising 47.76 mM of polyethylene glycol 3350, 230.68 mM of ascorbic acid, 47.47 mM of sodium ascorbate, 126.76 mM of sodium sulfate, 46.15 mM of sodium chloride, and 13.41 mM of potassium chloride.

The present invention provides the bowel cleansing solution comprising 160 g/L of polyethylene glycol 3350, 40.6 g/L of ascorbic acid, 9.4 g/L of sodium ascorbate, 18 g/L of sodium sulfate as an anhydride, 2.7 g/L of sodium chloride, and 1 g/L of potassium chloride.

The present invention provides the bowel cleansing composition comprising polyethylene glycol, ascorbate ingredients, sulfate, sodium chloride, and potassium chloride, in which the content of polyethylene glycol may be 144 to 176 g or 152 to 168 g, the content of ascorbate ingredients may be 45 to 55 g or 47.5 to 52.5 g, the content of sulfate may be 16.2 to 19.8 g or 17.1 to 18.9 gas an anhydride, the content of sodium chloride may be 2.43 to 2.97 g or 2.57 to 2.84 g, and the content of potassium chloride may be 0.9 to 1.1 g or 0.95 to 1.05.

When the ascorbate ingredients are ascorbic acid and sodium ascorbate, the content of ascorbic acid may be 36.54 to 44.66 g or 38.75 to 42.63 g, and the content of sodium ascorbate may be 8.46 to 10.34 g or 8.93 to 9.87 g. The sulfate may be sodium sulfate.

The present invention provides the bowel cleansing solution comprising polyethylene glycol, ascorbate ingredients, sulfate, sodium chloride, and potassium chloride, in which the content of polyethylene glycol may be 144 to 176 g/L or 152 to 168 g/L, the content of ascorbate ingredients may be 45 to 55 g/L or 47.5 to 52.5 g/L, the content of sulfate may be 16.2 to 19.8 g/L or 17.1 to 18.9 g/L as an anhydride, the content of sodium chloride may be 2.43 to 2.97 g/L or 2.57 to 2.84 g/L, and the content of potassium chloride may be 0.9 to 1.1 g/L or 0.95 to 1.05/L. When the ascorbate ingredients are ascorbic acid and sodium ascorbate, the content of ascorbic acid may be 36.54 to 44.66 g/L or 38.75 to 42.63 g/L, and the content of sodium ascorbate may be 8.46 to 10.34 g/L or 8.93 to 9.87 g/L. The sulfate may be sodium sulfate.

The bowel cleansing composition or the bowel cleansing solution of the present invention may further include a sweetening agent, and/or flavoring agent and the like as an additive.

The sweetening agent may be used in combination of one or more selected from the group consisting of saccharin, saccharin sodium, xylitol, sorbitol, mannitol, maltitol, lactitol, isomalt, stevioside, erythritol, aspartame, acesulfame potassium, and sucralose that exhibit sweetening effect and fast solubility even in a small amount, in addition to glucose, sucrose, dextrose, fructose and maltose, which are conventional sugars.

The sweetening agent may be contained in an amount of 0.03 to 3 parts by weight based on 100 parts by weight of polyethylene glycol.

In addition, the flavoring agent may be further contained in addition to the sweetening agent to improve patient compliance. The flavoring agent may be contained in an amount of 0.01 to 3 parts by weight based on 100 parts by weight of polyethylene glycol, and may be contained in the form of liquid, powder or clathrate.

The bowel cleansing solution of the present invention may be a solution containing sodium ions (Na+), potassium ions (K+) and/or chloride ions (Cl−).

In this case, the concentration of sodium ions may be 200 to 500 mEq/L, specifically 300 to 400 mEq/L, the concentration of potassium ions may be 5 to 30 mEq/L, specifically 10 to 20 mEq/L, and the concentration of chloride ions may be 30 to 90 mEq/L, specifically 40 to 80 mEq/L.

The concentration of sodium ions in the bowel cleansing solution of the present invention may be 400 mEq/L or less, specifically 370 mEq/L or less, and more specifically 350 mEq/L or less, the concentration of potassium ions may be 20 mEq/L or less, specifically 16 mEq/L or less, and more specifically 14 mEq/L or less, and the concentration of chloride ions may be 80 mEq/L or less, specifically 70 mEq/L or less, and more specifically 60 mEq/L or less.

The bowel cleansing solution containing high concentrations of sodium may present serious problems with regard to safety, drinkability and compliance, and the bowel cleansing solution of the present invention can solve such problems by including a suitable range of electrolytes. It is also important to provide the bowel cleansing solution with an appropriate concentration of electrolyte ions because hypersorption of ascorbate ingredients by sodium ions and hypersorption of sodium by chloride ions can occur.

The bowel cleansing solution of the present invention is hypertonic. The osmolality of the bowel cleansing solution may be provided as an experimental value or a theoretical value.

The theoretical value of osmolality of the bowel cleansing solution of the present invention may be 700 to 1100 mOsmol/kg, specifically 800 to 1000 mOsmol/kg, and more specifically 850 to 900 mOsmol/kg. The theoretical value of osmolality is a value calculated based on ingredients constituting the bowel cleansing solution of the present invention, and may be calculated as follows:

Theoretical value of osmolality (mOsmol/kg)=Σ{Amount of solute contained in solution (mg)/Molecular weight of solute*Dissociation constant (number of species produced per 1 mol of solute)}

As an example, the theoretical value of osmolality of the bowel cleansing composition of the present invention is calculated as shown in Table 1 below.

TABLE 1

| Ingredients | Molecular weight (MW) | Content (g) | Dissociation constant | Theoretical value of osmolality (mOsmol/kg) |
|---|---|---|---|---|
| PEG3350 | 3350 | 160 | 1 | 160 * 1000/3350 * 1 = 48 |
| $Na_2SO_4$ | 142 | 18 | 3 | 18 * 1000/142 * 3 = 380 |
| NaCl | 58.5 | 2.7 | 2 | 2.7 * 1000/58.5 * 2 = 92 |
| KCl | 74.55 | 1 | 2 | 1 * 1000/74.55 * 2 = 27 |
| Sodium ascorbate | 198 | 9.4 | 2 | 9.4 * 1000/198 * 2 = 95 |
| Ascorbic acid | 176 | 40.6 | 1 | 40.6 * 1000/176 * 1 = 231 |
| Total | | | | 873 |

However, the theoretical value of osmolality is not necessarily the same as the experimental value of osmolality which is actually measured, and may vary depending on the bowel cleansing solution to be measured. The experimental value of osmolality of the bowel cleansing solution of the present invention may be 1000 to 2000 mOsmol/kg, specifically 1200 to 1800 mOsmol/kg, and more specifically 1400 to 1700 mOsmol/kg. The experimental value of osmolality of the bowel cleansing solution of the present invention may be measured by using a freezing point depression method, but is not limited thereto.

In addition, the osmolality of the bowel cleansing solution of the present invention can be provided as an estimated value, the range of the estimated value can be derived through experiments. The estimated value of osmolality of the bowel cleansing solution of the present invention may be 1000 to 2000 mOsmol/kg, specifically 1300 to 1800 mOsmol/kg, and more specifically 1400 to 1700 mOsmol/kg. The estimated value of osmolality is a value capable of correcting a difference between theoretical value and experimental value and is a value taking into account the weighted value of osmotic force in the bowel cleansing solution of polyethylene glycol. The estimated value of osmolality may be calculated as follows.

Estimated value of osmolality (mOsmol/kg)={amount of polyethylene glycol contained in solution (mg)/molecular weight of polyethylene glycol*Dissociation constant (number of species produced per 1 mol of polyethylene glycol) *Weighted value (10% of amount of polyethylene glycol (g))}+{amount of sulfate contained in solution (mg)/molecular weight of sulfate*Dissociation constant (number of species produced per 1 mol of sulfate)}+{amount of sodium chloride contained in solution (mg)/molecular weight of sodium chloride*Dissociation constant (number of species produced per 1 mol of sodium chloride)}+{amount of potassium chloride contained in solution (mg)/molecular weight of potassium chloride*Dissociation constant (number of species produced per 1 mol of potassium chloride)}+{amount of ascorbic acid contained in solution (mg)/molecular weight of ascorbic acid*Dissociation constant (number of species produced per 1 mol of ascorbic acid)}+{amount of salts of ascorbic acid contained in solution (mg)/molecular weight of salts of ascorbic acid*Dissociation constant (number of species produced per 1 mol of salts of ascorbic acid)}

As an example, the estimated value of osmolality of the bowel cleansing solution of the present invention may be calculated as shown in Table 2 below.

TABLE 2

| Ingredients | Molecular weight (MW) | Content (g) | Dissociation constant | Weighted value | Estimated value of osmolality (mOsmol/kg) |
|---|---|---|---|---|---|
| PEG3350 | 3350 | 160 | 1 | 16 | 160 * 1000/3350 * 1 * 16 = 764 |
| $Na_2SO_4$ | 142 | 18 | 3 | — | 18 * 1000/142 * 3 = 380 |
| NaCl | 58.5 | 2.7 | 2 | — | 2.7 * 1000/58.5 * 2 = 92 |
| KCl | 74.55 | 1 | 2 | — | 1 * 1000/74.55 * 2 = 27 |
| Sodium ascorbate | 198 | 9.4 | 2 | — | 9.4 * 1000/198 * 2 = 95 |
| Ascorbic acid | 176 | 40.6 | 1 | — | 40.6 * 1000/176 * 1 = 231 |
| Total | | | | | 1589 |

The bowel cleansing composition or solution of the present invention, in which the weight ratio between polyethylene glycol and ascorbate ingredients is specified as 2.5:1 to 4:1 and ascorbate ingredients is specified as ascorbic acid and sodium ascorbate of the weight ratio of 3.5:1 to 5:1, is characterized by an excellent bowel-cleansing effect, while increasing safety. In one embodiment, it was confirmed that the bowel cleansing composition or solution of the present invention has an excellent bowel cleansing effect in an animal test (Experimental Examples 1 and 2) and has excellent safety due to less drastic changes in numerical values on a blood test (Experimental Example 2) compared to the composition or the solution having a different content ratios between polyethylene glycol and ascorbate ingredient or a different content ratio between ascorbic acid and sodium ascorbate in ascorbate ingredients, and has an excellent bowel cleansing effect and safety in clinical trials compared to Coolprep Powder, which is commercially available bowel cleansing composition (Experimental Example 3). And, it was confirmed that the bowel cleansing composition or solution of the present invention has excellent effects in both the convenience of taking (Experimental Example 4) and preference evaluation (Experimental Example 5) in clinical trials. The bowel cleansing composition of the present invention may be provided in various forms such as powders (powder, etc.), granules, tablets, capsules or liquids and the like, and each ingredient contained in the composition may be also provided in the same form or in different forms.

When the bowel cleansing composition is a solid preparation such as powders or granules, the composition may be dissolved in water to be taken, and when the bowel cleansing composition is provided as a tablets or capsules, it may be taken with a sufficient amount of water.

Each ingredient in the bowel cleansing composition of the present invention may be provided separately and/or packaged together. However, the ascorbate ingredients is preferably packaged separately from other ingredients depending on chemical properties.

In consideration of the following examples, it is preferable that the bowel cleansing composition of the present invention is appropriately packaged by dividing the total dose depending on the number of dose.

Specifically, the bowel cleansing composition of the present invention may be provided by packaging the total dose at a time, and may be provided by dividing the total dose into two or more packages.

The bowel cleansing composition of the present invention may be taken all the total dose at one time point (called non-split administration or split-dose administration on the day) or taken by dividing the total dose at several time points (called split-dose administration or two-day split-dose administration).

As an example of non-split administration (split-dose administration on the day), the bowel cleansing composition of the present invention may be taken over several hours in the evening before the test or in the morning of the test day. Specifically, a portion of the total dose may be taken, and after a certain time, for example, after 0.5 to 3 hours, taken the rest.

As an example of split-dose administration (or two-day split-dose administration), the bowel cleansing composition of the present invention may be taken a portion on the evening before the test, and the rest on the morning of the test day.

In taking the bowel cleansing composition, each dose may be taken within a certain period of time. Specifically, each dose may be taken within two hours, within one hour, or within 30 minutes.

The present invention provides the bowel cleansing composition and/or the bowel cleansing solution in which the bowel cleansing can be achieved enough to perform the test even with a small dose of the bowel cleansing agent, and the bowel cleansing solution of the present invention may be taken at a dose of about 1200 mL or less, specifically 1100 mL or less, and more specifically 1000 mL or less.

In addition, additional water may be taken after taking the bowel cleansing solution. Specifically, after taking the bowel cleansing solution, a certain amount, for example, in a volume of 0.5 to 2 L, specifically 1 to 1.5 L, and more specifically 1 L or less, of water may be additionally taken. Such additional water may be taken after taking all of the bowel cleansing solution, and may be taken between taking the bowel cleansing solution.

The bowel cleansing composition of the present invention may be used for the treatment of constipation.

The present invention also provides a method for cleansing the bowels, comprising administering a therapeutically effective amount of the bowel cleansing composition to the individuals.

The present invention also provides a method for treating constipation, comprising administering a therapeutically effective amount of the bowel cleansing composition to the individuals.

Further, the present invention provides a use of the composition for manufacturing a medicament for cleansing the bowels or treating constipation.

Advantageous Effects

The bowel cleansing composition and solution of the present invention have a small dose for taking and have a good taste, thus improving the convenience of taking and drug compliance and exhibiting a safe and excellent bowel cleansing effect, and thus can be used as an effective bowel cleansing agent.

DESCRIPTION OF DRAWINGS

FIG. 1 is a view confirming that there is no stool present in a large intestine as a result of visually identifying a degree of bowel cleansing in the group administered with a bowel cleansing composition.

FIG. 2 is a view confirming that there is still stool present in a large intestine as a result of visually identifying a degree of bowel cleansing in the group not administered with a bowel cleansing composition.

MODE FOR INVENTION

Hereinafter, the present invention will be described in more detail through examples. However, these examples are for illustrative purpose only and the scope of the present invention is not limited thereto.

Preparation Example 1: Preparation of Bowel Cleansing Composition and Solution

The bowel cleansing composition of the present invention was prepared in Examples 1 to 4 in accordance with the ingredients and content as shown in the Table 3 below.

TABLE 3

| Ingredients (g) | Example 1 | Example 2 | Example 3 | Example 4 |
|---|---|---|---|---|
| PEG3350 | 160 | 140 | 150 | 170 |
| $Na_2SO_4$ | 18 | 16 | 17.5 | 18.5 |
| NaCl | 2.7 | 2.0 | 2.5 | 3.0 |
| KCl | 1.0 | 0.5 | 0.8 | 1.2 |
| Ascorbic acid | 40.6 | 36 | 39 | 43 |
| Sodium ascorbate | 9.4 | 8 | 9 | 10 |

The bowel cleansing compositions of the above table 3 were prepared in Examples 1 to 4 solutions by dissolving in water so that the volume of liquid medicine to be 1 L. The molar concentration (mM) of ingredients contained in the solutions of Examples 1 to 4 and the molar ratio of main ingredients therein are shown in Table 4 below.

TABLE 4

| Ingredients (mM) | Example 1 | Example 2 | Example 3 | Example 4 |
|---|---|---|---|---|
| PEG3350 | 47.76 | 41.79 | 44.78 | 50.75 |
| $Na_2SO_4$ | 126.76 | 112.68 | 123.24 | 130.28 |
| NaCl | 46.15 | 34.19 | 42.74 | 51.28 |
| KCl | 13.41 | 6.71 | 10.73 | 16.10 |
| Ascorbate ingredients | 278.16 | 244.95 | 267.05 | 294.82 |
| Molar ratio of PEG:ascorbate ingredient | 1:5.82 | 1:5.86 | 1:5.96 | 1:5.81 |
| Molar ratio of ascorbic acid:sodium ascorbate | 4.86:1 | 5.06:1 | 4.88:1 | 4.84:1 |
| Molar ratio of PEG:$Na_2SO_4$ | 1:2.65 | 1:2.70 | 1:2.75 | 1:2.57 |

The bowel cleansing compositions of Examples 1 to 4 may be provided in the form of including two pouches (pouch A not containing ascorbate ingredients and pouch B containing ascorbate ingredients), wherein the pouches A and B can be taken by dissolving in water to be 1 L together. For example, the bowel cleansing composition of Example 1 may be provided in the form of including the pouches A and B, as shown in the Table 5 below, and may be provided in the same manner in the case of the bowel cleansing compositions of Examples 2 to 4.

TABLE 5

| Pouch A | | | | Pouch B |
|---|---|---|---|---|
| PEG3350 | $Na_2SO_4$ | NaCl | KCl | Ascorbate ingredients |
| 160 | 18 | 2.7 | 1.0 | 50 |

In addition, the bowel cleansing compositions of Examples 1 to 4 may be provided in the form of including four pouches (pouches A(1) and A(2) not containing ascorbate ingredients and pouches B(1) and B(2) containing ascorbate ingredients), wherein the pouches A(1) and B(1) can be taken by dissolving in water to be 500 mL together, and the pouches A(2) and B(2) can be taken by dissolving in water to be 500 mL together. For example, the bowel cleansing composition of Example 1 may be provided in the form of including the pouches A(1), A(2), B(1) and B(2), as shown in Tables 6 and 7 below, and the bowel cleansing compositions of Examples 2 to 4 may also be provided in the same manner.

TABLE 6

| Pouch A(1) | | | | Pouch B(1) |
|---|---|---|---|---|
| PEG3350 | $Na_2SO_4$ | NaCl | KCl | Ascorbate ingredients |
| 80 | 9 | 1.35 | 0.5 | 25 |

TABLE 7

| Pouch A(2) | | | | Pouch B(2) |
|---|---|---|---|---|
| PEG3350 | $Na_2SO_4$ | NaCl | KCl | Ascorbate ingredients |
| 80 | 9 | 1.35 | 0.5 | 25 |

Further, the bowel cleansing compositions of Examples 1 to 4 may be provided in the form of including the following eight pouches (pouches A(1), A(2), A(3) and A(4) not containing ascorbate ingredients and pouches B(1), B(2), B(3) and B(4) containing ascorbate ingredients), wherein the pouches A(1) and B(1) can be taken by dissolving in water to be 250 mL together, while in the same manner, the pouches A(2) and B(2), the pouches A(3) and B(3), and the pouches A(4) and B(4) can be taken by dissolving in water to be 250 mL together, respectively. Alternatively, the pouches A(1), A(2), B(1) and B(2) can be taken by dissolving in water to be 500 mL together, while the pouches A(3), A(4), B(3) and B(4) can be taken by dissolving in water to be 500 mL together. For example, the bowel cleansing composition of Example 1 may be provided in the form of including the pouches A(1), A(2), A(3), A(4), B(1), B(2), B(3) and B(4), as shown in Tables 8 to 11 below, and the bowel cleansing compositions of Examples 2 to 4 may also be provided in the same manner.

TABLE 8

| Pouch A(1) | | | | Pouch B(1) |
|---|---|---|---|---|
| PEG3350 | $Na_2SO_4$ | NaCl | KCl | Ascorbate ingredients |
| 40 | 4.5 | 0.675 | 0.25 | 12.5 |

TABLE 9

| Pouch A(2) | | | | Pouch B(2) |
|---|---|---|---|---|
| PEG3350 | $Na_2SO_4$ | NaCl | KCl | Ascorbate ingredients |
| 40 | 4.5 | 0.675 | 0.25 | 12.5 |

TABLE 10

| Pouch A(3) | | | | Pouch B(3) |
|---|---|---|---|---|
| PEG3350 | Na$_2$SO$_4$ | NaCl | KCl | Ascorbate ingredients |
| 40 | 4.5 | 0.675 | 0.25 | 12.5 |

TABLE 11

| Pouch A(4) | | | | Pouch B(4) |
|---|---|---|---|---|
| PEG3350 | Na$_2$SO$_4$ | NaCl | KCl | Ascorbate ingredients |
| 40 | 4.5 | 0.675 | 0.25 | 12.5 |

Mode for Invention

Experimental Example 1: Confirmation of Bowel Cleansing Effect in Animal Model

An animal model was used to confirm the bowel cleansing effect of the bowel cleansing solution of the present invention. Specifically, 20 mL of the bowel cleansing solution of Example 1 was administered to Sprague-Dawley rats. The rat was exsanguinated and sacrificed in six hours after starting the administration. Thereafter, the large intestine part was removed to check the degree of bowel cleansing.

As a result of confirming the degree of bowel cleansing in the group administered with the bowel cleansing solution and the group not administered with the same, it was confirmed that stool present in the large intestine was well removed in the group administered with the bowel cleansing solution (FIG. 1). Bowel cleansing was well performed in all of the six rats administered with the bowel cleansing solution, and five of them were very excellent degree of bowel cleansing. On the other hand, it was confirmed that stool is still present in the large intestine of the group not administered with the bowel cleansing solution (FIG. 2).

Through this, it was found that the bowel cleansing solution of the present invention exhibits very excellent bowel cleansing effect.

Experimental Example 2: Comparison of Bowel Cleansing Effect and Safety in Animal Model In order to confirm the effect depending on the composition of the bowel cleansing solution of the present invention, a comparative bowel cleansing solution was prepared to compare the bowel cleansing effect and safety in an animal model.

The ingredients and content of the compositions of Example 1 and Comparative Examples 1 to 4 are shown in Table 12 below, and were prepared by dissolving in water so that the total volume of the liquid medicine to be 1 L.

TABLE 12

| Ingredients (g) | Example 1 | Comparative Example 1 | Comparative Example 2 | Comparative Example 3 | Comparative Example 4 |
|---|---|---|---|---|---|
| PEG3350 | 160 | 80 | 160 | 160 | 160 |
| Na$_2$SO$_4$ | 18 | 18 | 18 | 18 | 18 |
| NaCl | 2.7 | 2.7 | 2.7 | 2.7 | 2.7 |
| KCl | 1.0 | 1.0 | 1.0 | 1.0 | 1.0 |
| Ascorbic acid | 40.6 | 83.32 | 24.48 | 19.58 | 7.34 |
| Sodium ascorbate | 9.4 | 19.29 | 27.54 | 33.05 | 46.82 |
| Total volume of liquid medicine | | | 1 L | | |

The molar concentrations of ingredients of the solution for bowel cleansing according to the above Table 12 are shown in Table 13 below.

TABLE 13

| Ingredients (mM) | Example 1 | Comparative Example 1 | Comparative Example 2 | Comparative Example 3 | Comparative Example 4 |
|---|---|---|---|---|---|
| PEG3350 | 47.76 | 23.88 | 47.76 | 47.76 | 47.76 |
| Na$_2$SO$_4$ | 126.76 | 126.76 | 126.76 | 126.76 | 126.76 |
| NaCl | 46.15 | 46.15 | 46.15 | 46.15 | 46.15 |
| KCl | 13.41 | 13.41 | 13.41 | 13.41 | 13.41 |
| Ascorbate ingredients | 278.16 | 570.83 | 278.18 | 278.17 | 278.17 |
| Molar ratio of PEG:ascorbate ingredient | 1:5.82 | 1:23.9 | 1:5.82 | 1:5.82 | 1:5.82 |
| Molar ratio of ascorbic acid:sodium ascorbate | 4.86:1 | 4.86:1 | 1:1 | 1:1.5 | 1:5.67 |
| Molar ratio of PEG:Na$_2$SO$_4$ | 1:2.65 | 1:5.31 | 1:2.65 | 1:2.65 | 1:2.65 |

The bowel cleansing effect of solutions of Example and Comparative Example was measured by using a rat animal model in the same manner as shown in Experimental Example 1. In order to objectively evaluate the bowel cleansing effect, the grade of bowel cleansing effect was measured based on the criteria as shown in Table 14 below. The criteria was based on Harefield Cleansing Scale which is widely used as the criteria for measurement of the degree of bowel preparation in clinical trials. The degree of bowel preparation of rats was evaluated by dividing into 1 to 5 grades.

TABLE 14

| Grade | Criteria |
| --- | --- |
| Grade 1 | Only clean or transparent liquid is present |
| Grade 2 | Small amount of brown liquid is present, with little semi-solid stool |
| Grade 3 | Brown liquid, completely removable semi-solid stool is present |
| Grade 4 | Partially removable semi-solid stool is present |
| Grade 5 | Irremovable, hard stool is present |

Comparison of Bowel Cleansing Effect and Safety According to Content Ratio Between Polyethylene Glycol and Ascorbate Ingredients The solution of Comparative Example 1 in Tables 12 and 13 had a polyethylene glycol content (80 g) that is half of the solution of Example 1 (160 g), while the concentration of ascorbate ingredients (570.83 mM) is about double of the solution of Example 1 (278.16 mM). After the oral administration of the solution of Example 1 (n=6) and the solution of Comparative Example 1 (n=6) to 12 rats, the degree of bowel preparation was evaluated according to criteria of the Table 14 and the results are shown in Table 15 below.

TABLE 15

| | Degree of bowel cleansing (n) | | | | |
| --- | --- | --- | --- | --- | --- |
| | Grade 1 | Grade 2 | Grade 3 | Grade 4 | Grade 5 |
| Example 1 | 3 | 2 | 1 | 0 | 0 |
| Comparative Example 1 | 0 | 3 | 2 | 1 | 0 |

As can be seen from the above table, it can be seen that the bowel cleansing effect according to the content of polyethylene glycol and ascorbate ingredients of the solution of Example 1 is outstandingly excellent. In addition, in order to measure the safety when taking the bowel cleansing solution, a blood test was performed on rats taking the solution of Example 1 and the solution of Comparative Example 1. In the group of animals taking the solution of Comparative Example 1, a dead individual occurred and gastric mucosal injury was observed. In contrast, in the group of animals taking the solution of Example 1, there is no dead individual. As a result of measuring a concentration of asparate aminotransferase (AST), alkaine aminotransferase (ALT), blood urea nitrogen (BUN), creatinine, red blood cell (RBC), hemoglobin (HGB), mean corpuscular hemoglobin concentration (MCHC), hematocrit (HCT), etc. in a blood test, it was confirmed that numerical changes were significantly low in the individuals taking the solution of Example 1 than those of individuals taking the solution of Comparative Example 1, thereby exhibiting more excellent safety.

From the above results, it can be seen that the bowel cleansing solution of the present invention according to the content ratio of polyethylene glycol and ascorbate ingredient is excellent in both bowel cleansing effect and safety, and can be usefully used as a solution for bowel cleansing.

Comparison of Bowel Cleansing Effect and Safety According to Molar Ratio Between Ascorbic Acid and Sodium Ascorbate The solution of Comparative Example 2 and Example 1 of Tables 12 and 13 have the same content of polyethylene glycol and ascorbate ingredients. However, the solution of Example 1 had a molar ratio between ascorbic acid and sodium ascorbate contained in the ascorbate ingredients of about 4.86:1, while the solution of Comparative Example 2 had a molar ratio of 1:1, and the molar ratio is different from each other.

With regard to a total of 12 rats, the degree of bowel preparation of groups taking Example 1 (n=6) and Comparative Example 2 (n=6) was measured according to the criteria of Table 14, and the results are shown in Table 16 below.

TABLE 16

| | Degree of bowel cleansing (n) | | | | |
| --- | --- | --- | --- | --- | --- |
| | Grade 1 | Grade 2 | Grade 3 | Grade 4 | Grade 5 |
| Example 1 | 3 | 2 | 1 | 0 | 0 |
| Comparative Example 2 | 0 | 1 | 5 | 0 | 0 |

The solutions of Comparative Examples 3 and 4 and Example 1 of Tables 12 and 13 have the same content of polyethylene glycol and ascorbate ingredients. However, the solution of Example 1 had a molar ratio between ascorbic acid and sodium ascorbate contained in the ascorbate ingredients of about 4.86:1, while the solutions of Comparative Examples 3 and 4 have a molar ratio of 1:1.5 and 1:5.67, respectively, and the molar ratio are different from each other.

With regard to a total of 18 rats, the degree of bowel preparation of groups taking Example 1 (n=6), Comparative Example 3 (n=6) and Comparative Example 4 (n=6) was measured according to the criteria of Table 14, and the results are shown in Table 17 below.

TABLE 17

| | Degree of bowel cleansing (n) | | | | |
| --- | --- | --- | --- | --- | --- |
| | Grade 1 | Grade 2 | Grade 3 | Grade 4 | Grade 5 |
| Example 1 | 4 | 1 | 1 | 0 | 0 |
| Comparative Example 3 | 0 | 3 | 3 | 0 | 0 |
| Comparative Example 4 | 0 | 3 | 3 | 0 | 0 |

As can be seen from the above table, it can be seen that the solutions of Example 1 and Comparatives Examples 2, 3 and 4 contain the same amount of polyethylene glycol and ascorbate ingredients, but the solution of Example 1 has more excellent bowel cleansing ability compared to the solutions of Comparative Examples 2, 3 and 4, which have different ratio between ascorbic acid and sodium ascorbate. Further, a blood test was performed on rats taking the solution of Example 1 and the solutions of Comparative Examples 2, 3 and 4, in order to measure the safety when taking the bowel cleansing solution. As a result, it was confirmed that the numerical changes of AST and NA+ in the blood of rats taking the solutions of Comparative Examples 2, 3 and 4 were much higher than those of rats taking the solution of Example 1. It was confirmed that the solution of Example 1 is a bowel cleansing solution having higher safety compared to the solutions of Comparative Examples 2, 3 and 4.

From the above results, it can be seen that the bowel cleansing solution of the present invention according to a content ratio between ascorbic acid and sodium ascorbate is excellent in both bowel cleansing effect and safety, and thus it can be usefully used as a solution for bowel cleansing.

Experimental Example 3: Comparison of Bowel Cleansing Effect and Safety in Clinical Trials After the administration of the bowel cleansing solution of Example 1 and Coolprep Powder, a commercial product, to a patient group which is randomly selected, the bowel cleaning effect was confirmed. The bowel cleansing solution of Example 1 was taken in a volume of 1 L, and Coolprep Powder is a product that is taken in a volume of 2 L as a liquid medicine. The composition of Example 1 and Coolprep Powder is shown in Table 18 below.

TABLE 18

| Ingredients | Example 1 (g) | Coolprep Powder (g) |
|---|---|---|
| PEG3350 | 160 | 200 |
| $Na_2SO_4$ | 18 | 15 |
| NaCl | 2.7 | 5.38 |
| KCl | 1.0 | 2.03 |
| Ascorbic acid | 40.6 | 9.4 |
| Sodium ascorbate | 9.4 | 11.8 |
| Volume of liquid medicine | 1 L | 2 L |

The patient group was divided into three, and taking the bowel cleansing solution of Example 1 on the day of colonoscopy (split-dose administration on the day, Test Group 1), taking the bowel cleansing solution of Example 1 by dividing into the day before colonoscopy and the day of colonoscopy (two-day split-dose administration, Test Group 2), and taking Coolprep Powder by dividing into the day before colonoscopy and the day of colonoscopy (two-day split-dose administration, Test Group 3), respectively. Specifically, Test Group 1 was taken 500 mL of the bowel cleansing solution of Example 1 for about 30 minutes, then taken 500 mL of the bowel cleansing solution of Example 1 for about 30 minutes in about one to two hours later, and then further taken 1 L of water. After taking the bowel cleansing solution, water was divided into 500 mL and drink.

Test Groups 2 and 3 were taken 500 mL of the bowel cleansing solution of Example 1 (for about 30 minutes) and 1 L of Coolprep Powder (for about 1 hour) in the evening of the day before the test, respectively, and taken 500 mL of water, and then taken 500 mL of the bowel cleansing solution of Example 1 (for about 30 minutes) and 1 L of Coolprep Powder (for about one hour) in the morning of the day of test and taken 500 mL of water.

The Bowel cleansing results were evaluated on Harefield Cleansing Scale, with Grades A and B being successful in the bowel cleansing, and Grades C and D being failure in the bowel cleansing. Grade A is a case where all parts of the large intestine (rectum, S-colon, descending colon, transverse colon, and ascending colon) are in an "empty and clean" or a state of "transparent liquid," which means the very excellent degree of bowel preparation.

As a result of bowel cleansing, the success rate of the test group taking the bowel cleansing solution of Example 1 was higher than that of the test group taking Coolprep Powder, and the number of patients evaluated as Grade A was greater than Test Group 3 much more in Test Groups 1 and 2. In particular, comparing Test Groups 2 and 3 applying the same method of taking, it can be seen that the evaluation rate of Grade A in Test Group 2 is 80.00%, which is much higher than 55.21% of Test Group 3.

TABLE 19

| Patient Group | | Test Group 1 | Test Group 2 | Test Group 3 |
|---|---|---|---|---|
| Number of Patients | | 94 | 95 | 96 |
| Bowel cleansing agent | | Bowel cleansing solution of Example 1 | Bowel cleansing solution of Example 1 | Coolprep Powder |
| Method of taking | | Split-dose administration on the day | Split-dose administration | Split-dose administration |
| Number of patients for each grade of bowel preparation | A | 62 (65.96%) | 76 (80.00%) | 53 (55.21%) |
| | B | 29 (30.85%) | 18 (18.95%) | 38 (39.58%) |
| | C | 3 (3.19%) | 0 (0%) | 5 (5.21%) |
| | D | 0 (0.00%) | 1 (1.05%) | 0 (0.00%) |
| Ratio of successful patients | | 96.81% | 98.95% | 94.79% |

TABLE 20

| | Ratio of patients with Grade A | | |
|---|---|---|---|
| | Test Group 1 | Test Group 2 | Test Group 3 |
| Ascending colon | 75.53% (71/94) | 83.16% (79/95) | 62.50% (60/96) |
| Transverse colon | 88.30% (83/94) | 94.74% (90/95) | 76.04% (73/96) |
| Descending colon | 92.55% (87/94) | 90.53% (86/95) | 82.29% (79/96) |
| S-colon | 87.23% (82/94) | 89.47% (85/95) | 81.25% (78/96) |
| Rectum | 91.49% (86/94) | 92.63% (88/95) | 80.21% (77/96) |

As a result of comparing the rates at which the degree of bowel preparation was evaluated as Grade A in each part of large intestine (rectum, S-colon, descending colon, transverse colon, and ascending colon), the rate in Test Group 1 or 2 patient group was higher than that of Test Group 3 patient group. In particular, ascending colon has a high risk of serrated polyp, in which Test Groups 1 and 2 showed significantly more excellent degree of bowel preparation in the ascending colon compared to Test Group 3.

In addition, considering that the bowel cleansing composition of Example 1 was taken in a volume of 1 L only as a liquid medicine while Coolprep Powder is a product that is taken in a volume of 2 L as a liquid medicine, it can be seen that the bowel cleansing composition of the present invention showed an excellent bowel cleansing effect than that of the commercial product.

The degree of bowel preparation is very important to determine the accuracy of the colonoscopy, and the bowel cleansing composition of the present invention is a composition having a more excellent bowel cleansing ability compared to Coolprep Powder, the commercial product, and having an excellent effect of increasing accuracy of colonoscopy and disease diagnosis.

Further, it was confirmed that there is no problem in the safety such as imbalance of electrolytes (Na+, etc.), etc., by taking the bowel cleansing solution of Example 1.

From the above results, it can be seen that the bowel cleansing solution of the present invention is clinically excellent in both bowel cleansing effect and safety and thus can be usefully used as a bowel cleansing solution.

Experimental Example 4: Evaluation of the Convenience of Taking in Clinical Trials In case it is difficult to take a sufficient amount of solution as required to achieve a bowel cleansing effect even if the bowel cleansing effect is excellent, due to the characteristics of taking an excessive amount of solution, there is a problem that it is difficult to achieve the desired effect.

Accordingly, the bowel cleansing solution of Example 1 was taken on the day of colonoscopy (Test Group 1, N=94) or the bowel cleansing solution of Example 1 was taken by dividing on the day before colonoscopy and the day of colonoscopy (Test Group 2, N=95), after which an evaluation was made on completion rate of taking, medication compliance, ease of completion of taking, intention to reuse and taste.

All patients in Test Groups 1 and 2 took the bowel cleansing solution of Example 1 and the completion rate of taking was 100%. As a result of evaluating medication compliance (=Dose taken/Scheduled dose*100), all the patients of Test Groups 1 and 2 took the bowel cleansing solution at 75% or more, thereby confirming excellent compliance to medication.

The ease of completion of taking to the patients who took the bowel cleansing solution of Example 1 was evaluated by categorizing "Yes" or "No." As a result, all the patients excluding one in Test Group 1 and all the patients of Test Group 2 answered "Yes."

The intention to reuse of taking to the patients who took the bowel cleansing solution of Example 1 was evaluated by categorizing "Yes" or "No." As a result, 70% or more of Test Group 1 and 80% or more of Test Group 2 answered "Yes."

As a result of the taste of the bowel cleansing solution of Example 1, the patients who answered "Good" or "Fine" were 80% and 87% in Test Groups 1 and 2, respectively, and the patients who answered "Very Bad" were 4% and 1% in Test Groups 1 and 2, respectively.

As a result of evaluation, the bowel cleansing solution of Example 1 was evaluated as being very excellent in both completion rate of taking and medication compliance, being easy to take, and being excellent in both intention to reuse and taste.

Experimental Example 5: Evaluation of Preference

Since the bowel cleansing requires taking a considerable amount of solution required for sufficient bowel preparation, it is important to provide a bowel cleansing solution with higher preference for taking. Preference evaluation was performed for the bowel cleansing solution with different content ratios between ascorbic acid and sodium ascorbate.

The bowel cleansing solution was prepared by dissolving the compositions of Example 1 and Comparative Examples 2 and 5 in water so that a total volume of liquid medicine to be 1 L, and the specific composition is shown in Table 21 below.

TABLE 21

| Ingredients (g) | Example 1 | Comparative Example 2 | Comparative Example 5 |
|---|---|---|---|
| PEG3350 | 160 | 160 | 160 |
| $Na_2SO_4$ | 18 | 18 | 18 |
| NaCl | 2.7 | 2.7 | 2.7 |
| KCl | 1.0 | 1.0 | 1.0 |
| Ascorbic acid | 40.6 | 24.48 | 8.35 |
| Sodium ascorbate | 9.4 | 27.54 | 45.67 |
| Volume of liquid medicine | | 1 L | |

The molar ratio between ascorbic acid and sodium ascorbate contained in the solutions of the Example 1 and Comparative Examples 2 and 5 were 4.86:1, 1:1 and 1:4.86 respectively, and the molar concentration of ascorbate ingredients contained in each solution was about 278 mM. The same amount of additives (flavoring agent and sweetening agent) was contained in the bowel cleansing solutions used for evaluating preference. A total of 96 patients tasted 20 mL of the solutions of Example 1 and Comparative Examples 2 and 5, respectively, and evaluated the preference as 1st (1 point), 2nd (2 points) and 3rd (3 points) (ranking method). And then, preference scores were summed up to perform a t-test verification. As a total preference score becomes lower, preference gets higher.

As a result of the evaluation, the preference scores for the solutions of Example 1 and Comparative Examples 2 and 5 were 174, 204, and 198 points, respectively, in which the preference for the solution of Example 1 was the highest. As a result of t-test verification (reliability of 95%), it was confirmed that the preference for the solution of Example 1 shows a significant difference for the preferences for the solutions of Comparative Examples 2 and 5 (p=0.00554 and p=0.04521). Accordingly, it can be seen that the composition having a high content ratio of ascorbic acid according to the present invention is a composition having a more excellent preference for taking.

The present specification omits the details that those skilled in the art of the present invention can fully recognize and infer, and various modifications can be made more within a range that does not change the technical spirit or essential constitution of the present invention in addition to the specific examples described herein. Thus, the present invention may be implemented in a different manner from those specifically described and exemplified in the present specification, which may be understood by those skilled in the technical field of the present invention.

The invention claimed is:

1. A bowel cleansing composition comprising polyethylene glycol (PEG) and ascorbate ingredients, wherein a weight ratio between polyethylene glycol and ascorbate ingredients is 2.5:1 to 4:1, a content of polyethylene glycol ingredients is 140 g to 180 g, a content of ascorbate ingredients is 45 g or more and less than 55 g, and the ascorbate ingredients comprise ascorbic acid and sodium ascorbate at a weight ratio of 3.5:1 to 5:1, wherein the composition is in the form of tablet, granule, powder, capsule or liquid.

2. The bowel cleansing composition according to claim 1, wherein the content of ascorbic acid is 35 to 45 g and the content of sodium ascorbate is 8 to 11 g.

3. The bowel cleansing composition according to claim 1, comprising sodium sulfate, wherein a weight ratio between polyethylene glycol and sodium sulfate is 7:1 to 12:1.

4. The bowel cleansing composition according to claim 3, wherein a content of sodium sulfate is 16 to 20 g as an anhydride.

5. The bowel cleansing composition according to claim 1, comprising 2 to 3.5 g of sodium chloride.

6. The bowel cleansing composition according to claim 1, comprising 0.5 to 2 g of potassium chloride.

7. A bowel cleansing solution, comprising polyethylene glycol (PEG) and ascorbate ingredients, wherein a content ratio between polyethylene glycol and ascorbate ingredients is 2.5:1 to 4:1, a content of polyethylene glycol is 140 g/L to 180 g/L, a content of ascorbate ingredients is 45 g/L or more and less than 55 g/L, and ascorbate ingredients comprise ascorbic acid and sodium ascorbate at a molar ratio of 4:1 to 6:1.

8. The bowel cleansing solution according to claim 7, wherein a content of ascorbic acid is 200 to 255 mM and a content of sodium ascorbate is 40 to 55 mM.

9. The bowel cleansing solution according to claim 7, comprising sulfate, wherein a molar ratio between polyethylene glycol and sulfate is 1:2 to 1:3.5.

10. The bowel cleansing solution according to claim 9, comprising 110 to 140 mM of sulfate.

11. The bowel cleansing solution according to claim 9, comprising 35 to 60 mM of sodium chloride.

12. The bowel cleansing solution according to claim 9, comprising 7 to 27 mM of potassium chloride.

13. The bowel cleansing solution according to claim 7, wherein a concentration of sodium ions is 200 to 500 mEq/L.

14. The bowel cleansing solution according to claim 12, wherein a concentration of potassium ions is 5 to 30 mEq/L.

15. The bowel cleansing solution according to claim 11, wherein a concentration of chloride ions is 30 to 90 mEq/L.

16. The bowel cleansing solution according to claim 7, wherein the bowel cleansing solution is hypertonic.

17. The bowel cleansing solution according to claim 7, wherein the bowel cleansing solution is taken at a dose of 1200 mL or less.

18. The bowel cleansing composition according to claim 1, wherein the average molecular weight of polyethylene glycol is 2,000 to 8,000.

19. The bowel cleansing composition according to claim 1, wherein the average molecular weight of polyethylene glycol is 3,000 to 4,000.

20. The bowel cleansing solution according to claim 7, wherein the average molecular weight of polyethylene glycol is 2,000 to 8,000.

21. The bowel cleansing solution according to claim 7, wherein the average molecular weight of polyethylene glycol is 3,000 to 4,000.

22. The bowel cleansing composition according to claim 1, wherein the bowel cleansing composition comprises: (i) 160 g of polyethylene glycol with the average molecular weight of 3,000 to 4,000, (ii) 40.6 g of ascorbic acid, (iii) 9.4 g of sodium ascorbate, (iv) 16 to 20 g of sodium sulfate, (v) 2 to 3.5 g of sodium chloride, and (vi) 0.5 to 2 g of potassium chloride.

23. The bowel cleansing solution according to claim 7, wherein the bowel cleansing solution comprises: (i) 160 g/L of polyethylene glycol with the average molecular weight of 3,000 to 4,000, (ii) 40.6 g/L of ascorbic acid, (iii) 9.4 g/L of sodium ascorbate, (iv) 16 to 20 g/L of sodium sulfate, (v) 2 to 3.5 g/L of sodium chloride, and (vi) 0.5 to 2 g/L of potassium chloride.

24. The bowel cleansing solution according to claim 11, wherein a concentration of sodium ions is 200 to 500 mEq/L.

25. The bowel cleansing solution according to claim 12, wherein a concentration of chloride ions is 30 to 90 mEq/L.

* * * * *

UNITED STATES PATENT AND TRADEMARK OFFICE
CERTIFICATE OF CORRECTION

| | |
|---|---|
| PATENT NO. | : 11,510,884 B2 |
| APPLICATION NO. | : 16/965182 |
| DATED | : November 29, 2022 |
| INVENTOR(S) | : Joon Youb Lee et al. |

It is certified that error appears in the above-identified patent and that said Letters Patent is hereby corrected as shown below:

In the Claims

Claim 10, Column 27, Line 43, "claim 9" should read --claim 7--;

Claim 11, Column 27, Line 45, "claim 9" should read --claim 7--; and

Claim 12, Column 28, Line 1, "claim 9" should read --claim 7--.

Signed and Sealed this
Twenty-first Day of February, 2023

*Katherine Kelly Vidal*

Katherine Kelly Vidal
*Director of the United States Patent and Trademark Office*